(12) United States Patent
Zhu et al.

(10) Patent No.: US 7,491,174 B2
(45) Date of Patent: Feb. 17, 2009

(54) DEVICE AND METHOD FOR PERFORMING ELECTRICAL IMPEDANCE TOMOGRAPHY

(75) Inventors: Fansan Zhu, Flushing, NY (US); Nathan W. Levin, New York, NY (US)

(73) Assignee: Renal Research Institute, LLC, New York, NY (US)

( * ) Notice: Subject to any disclaimer, the term of this patent is extended or adjusted under 35 U.S.C. 154(b) by 0 days.

(21) Appl. No.: 10/808,871

(22) Filed: Mar. 25, 2004

(65) Prior Publication Data

US 2004/0242989 A1 Dec. 2, 2004

Related U.S. Application Data

(60) Provisional application No. 60/457,667, filed on Mar. 25, 2003.

(51) Int. Cl.
*A61B 5/08* (2006.01)

(52) U.S. Cl. .................. 600/533; 600/529; 600/536

(58) Field of Classification Search ......... 600/407–434, 600/473, 476, 547, 533, 536, 529; 382/131; 606/130
See application file for complete search history.

(56) References Cited

U.S. PATENT DOCUMENTS

| | | | |
|---|---|---|---|
| 4,204,545 A | | 5/1980 | Yamakoshi |
| 4,370,983 A | | 2/1983 | Lichtenstein |
| 5,311,878 A | * | 5/1994 | Brown et al. ............. 600/547 |
| 5,449,000 A | | 9/1995 | Libke et al. |
| 5,580,460 A | | 12/1996 | Polaschegg |
| 6,015,389 A | * | 1/2000 | Brown ..................... 600/533 |
| 6,122,599 A | * | 9/2000 | Mehta ..................... 702/100 |
| 6,157,697 A | * | 12/2000 | Mertelmeier et al. ....... 378/37 |
| 6,228,033 B1 | | 5/2001 | Koobi et al. |

(Continued)

FOREIGN PATENT DOCUMENTS

EP 1 205 144 5/2002

(Continued)

OTHER PUBLICATIONS

"Newton-Raphson Method", Electrical Impedance Tomography, Reconstruction Algorithms, pp. 122-129.

(Continued)

*Primary Examiner*—Brian L. Casler
*Assistant Examiner*—Baisakhi Roy
(74) *Attorney, Agent, or Firm*—Kenyon & Kenyon LLP (57) ABSTRACT

A system for performing electrical impedance tomography. The system includes a first set of electrodes positioned in a first plane and a second set of electrodes positioned in a second plane. The system also includes a third set of electrodes positioned in a third plane between the first and second planes. The third set of electrodes is rotatable around an axis intersecting the third plane. Furthermore, the third set of electrodes may be moveable in an axial direction between the first and second planes to various other planes, e.g., a fourth plane, a fifth plane, etc. The processor is further configured to process the voltage measurements taken by the voltage measurement device so as to generate a current density distribution in the various other planes. In addition, the processor is further configured to generate a three-dimensional image corresponding to the current density distribution between the first and second planes.

29 Claims, 6 Drawing Sheets

U.S. PATENT DOCUMENTS

| | | | |
|---|---|---|---|
| 6,231,572 B1* | 5/2001 | Hart et al. | 606/45 |
| 6,236,886 B1* | 5/2001 | Cherepenin et al. | 600/547 |
| 6,246,894 B1 | 6/2001 | Steuer et al. | |
| 6,363,275 B1* | 3/2002 | Kaiser | 600/547 |
| 6,490,471 B2* | 12/2002 | Svenson et al. | 600/407 |
| 6,501,984 B1* | 12/2002 | Church et al. | 600/547 |
| 2003/0216630 A1* | 11/2003 | Jersey-Willuhn et al. | 600/407 |
| 2004/0097806 A1* | 5/2004 | Hunter et al. | 600/434 |
| 2004/0209351 A1* | 10/2004 | Thielecke et al. | 435/287.1 |

FOREIGN PATENT DOCUMENTS

| | | |
|---|---|---|
| GB | 2 069 706 | 8/1981 |
| WO | WO 92/19153 | 11/1992 |
| WO | WO 96/32883 | 10/1996 |
| WO | WO 98/51211 | 11/1998 |
| WO | WO 02/13691 | 2/2002 |

OTHER PUBLICATIONS

P.M. Kouw et al. "Assessment of post-dialysis dry weight: An application of the conductivity measurement method," Kidney Int., vol. 41 (1992), pp. 440-444.

Piccoli A. "Identification of Operational Clues to Dry Weight Prescription in Hemodialysis Using Bioimpedance Vector Analysis," Kidney Int., vol. 53 (1998), pp. 1036-1043.

J.P. de Vries et al. "Non-invasive Monitoring of Blood Volume During Hemodialysis: Its Relation to Post-dialytic Dry Weight," Kidney Int. vol. 44 (1993), pp. 851-854.

J.K. Leypoldt et al. "Determination of Circulating Blood Volume y Continuously Monitoring Hematocrit During Hemodinlysis," Journal Am. Soc. Nephrol. vol. 6 (1995), pp. 214-219.

J.K. Leypoldt et al. "Evaluating volume status in hemodialysis patients," Adv. Ren. Replace. Ther., vol. 5 (1998), pp. 64-74.

J.G. Webster. "Measurement of Flow and Volume of Blood," *Medical Instrumentation Application and Design*, Wiley, New York, 3$^{rd}$ Ed. (1998) pp. 357-371.

Shimazu et al., "Electric Impedance Cuff For the Indirect Measurement of Blood Pressure and Volume Elastic Modulus in Human Limb and Finger Arteries", Medical and Biological Engineering and Computing, Peter Peregrinus Ltd., Stevenage, GB, vol. 27, No. 5, Sep. 1, 1989, pp. 477-483.

Zhu et al., "Determination of Dry Weight in Hemodialysis Patients by Monitoring Changes in the Slope of Extracellular Volume (ECV) During Dialysis," ASAIO, vol. 48, No. 2 (2002), p. 180.

Zhu et al., "Estimation of Volume of Fluid in the Peritoneal Cavity by Bioimpedance Analysis", BMES/EMBS Conference, 1999, Proceedings of the First Joint Atlanta, GA, USA, Oct. 13-16, 1999.

Zhu et al., "Validation of Changes in Extra Cellular Volume Measured During Hemodialysis Using a Segmented Biopedance Technique", ASAIO Journal, 1998, pp. M541-M545.

* cited by examiner

DEVICE AND METHOD FOR PERFORMING ELECTRICAL IMPEDANCE TOMOGRAPHY

RELATED APPLICATIONS

The present application claims the benefit of priority to Applicant's U.S. Patent Provisional Patent Application Ser. No. 60/457,667, filed on Mar. 25, 2003.

BACKGROUND

Vascular access presents one of the major problems affecting the success of hemodialysis treatment. Currently, vascular access failure is a major cause of morbidity for hemodialysis patients. Graft access thrombosis occurs in 60% of patients within one year and more than 30% of all grafts fail within 18 months after placement. Vascular access complications are the major cause of morbidity in the hemodialysis population, accounting for more than 15% of hospitalizations.

To maximize the longevity of a vascular access, Kidney Disease Outcomes Quality Initiative, i.e., K/DOQI, practice guidelines suggest an aggressive policy for monitoring vascular access patency for the purpose of extending the life of a monitoring access and minimizing thrombosis. Conventional devices diagnose the presence of pathology by measuring parameters, such as access flow and access recirculation. These conventional devices may employ a variety of techniques, for instance ultrasound dilution techniques. However, these devices and methods provide only indirect evidence of the access site and of the degree of access pathology.

One technique for monitoring a vascular access is referred to as ultrasound Doppler imaging. The ultrasound Doppler imaging technique provides an image of the access flow, which provides different information than the dilution method. However, a major problem of the ultrasound Doppler imaging technique is operator error. For instance, this technique requires that measurements be taken at the same location of a patient at different times. There is significant difficulty in identifying the same location of the patient when a subsequent measurement is taken. Computerized X-ray tomography ("X-ray CT") is another technique for monitoring a vascular access to provide an image of an access area. However, both the ultrasound Doppler imaging technique and X-ray CT are expensive methods which cannot be routinely used in clinical practice. Further, these imaging techniques cannot continuously monitor a vascular access during hemodialysis.

Another technique for monitoring a vascular access is electrical impedance tomography. Electrical impedance tomography provides an image based on a distribution of conductivity in a cross sectional area. Since organs and fluid volume, such as blood, have very different conductivity, and since particularly vascular grafts have a relative lower conductivity than blood vessels, in the arm, vascular grafts can be easily identified by electrical impedance tomography. Moreover, a dynamic image of a vascular access can be obtained by electrical impedance tomography.

One advantage of electrical impedance tomography is the ability to continuously measure changes in blood flow in the regional area with much lower cost, easy operation and portability. For instance, relative to other techniques, e.g., X-ray CT and positron emission tomography, electrical impedance tomography is significantly less expensive to perform and smaller in size. In addition, electrical impedance tomography is non-invasive, and employs a very weak electrical current on the skin, e.g., 0.25-5 mA. Furthermore, because electrical impedance tomography may produce many, e.g., thousands, of images per second, electrical impedance tomography may be employed to measure and monitor a vascular access continuously.

One problem that is experienced with electrical impedance tomography is that, because electric current flow in the body does not progress in straight lines but rather tends to spread out in all directions, electrical impedance tomography provides low spatial resolution. In addition, electrical impedance tomography does not consist merely of information relating to a measurement plane, e.g., a plane of conductivity distribution at which a measurement is taken, but also includes significant contributions of information from outside the measurement plane.

One method that may be employed in order to improve the resolution of an image in a cross-sectional area, e.g., the cross-sectional area of a vascular access, is to increase in the number of electrodes in the same area. However, a large number of electrodes positioned on a limited circular surface, e.g., an inner circumference of a vascular access, will reduce the distance between adjacent electrodes. As a result, there may be significant errors in the measurements provided by the electrodes because of the effect of skin impedance on the measurements. This is especially problematic for the purpose of three dimensional imaging, which in conventional systems employs numerous electrodes in close proximity relative to each other. Errors of individual electrode location and the connecting interface between electrode and skin are major sources of measurement error that significantly reduce the resolution of an image generated by electrical impedance tomography.

Currently, there are two major models which are used to generate, e.g., reconstruct, an image. A first model that can be used to reconstruct an image is referred to as "the forward problem". In the first model, there is provided a resistivity distribution with a boundary current and voltage, and there is calculated the internal current and voltage distribution. To provide a solution to the forward problem, the first model employs a Finite Element Method ("FEM") algorithm that is used to reconstruct the image.

A second model that can be used to reconstruct an image is referred to as the 'problem'. In the second model, there is provided the boundary current and voltage and an internal resistivity distribution is calculated. To provide a solution to the inverse problem, the second model employs a back projection algorithm to calculate the resistivity distribution.

SUMMARY OF THE INVENTION

The present invention, in accordance with various embodiments thereof, relates to a system for performing electrical impedance tomography. The system includes a first set of electrodes positioned in a first plane and a second set of electrodes positioned in a second plane. The system also includes a third set of electrodes positioned in a third plane between the first and second planes. The third set of electrodes is rotatable around an axis intersecting the third plane. In one embodiment, the first, second and third sets of electrodes are mounted on upper and lower portions of an imaging device, the upper and lower portions being separable so as to enable a patient's body part to be positioned between the upper and lower portions and a vascular image of the body part to be obtained.

The system may include a current source configured to inject current between at least one electrode of the first set of electrodes and at least one electrode of the second set of electrodes. The current source may also be configured to inject current between a first electrode of the third set of electrodes and a second electrode of the third set of electrodes. In this embodiment, the system also includes one or more switches that are configured to selectively connect each one of the electrodes of the first set of electrodes to each one of the electrodes of the second set of electrodes. In addition, the system may include one or more switches that are configured to selectively connect one electrode of the third set of electrodes to the other electrodes of the third set of electrodes. A processor is configured to control the selective connection of the electrodes via the switches.

The system may also include a voltage measurement device configured to measure voltage between a first electrode of the third set of electrodes and a second, third, etc., electrode of the third set of electrodes. In this embodiment, one or more switches are employed to selectively connect a first electrode of the third set of electrodes and the other electrodes of the third set of electrodes to the voltage measurement device. A processor may be employed to control these switches. The voltage measurement device may be an amplifier.

In one embodiment, the third set of electrodes is supported by an electrode supporting unit which is configured to be rotatable within a housing. The electrode supporting unit may include a first biasing element for biasing the electrodes radially inward and a second biasing element for biasing the electrodes radially outward. In addition, the electrode may include a storage container for conductive gel, the electrode being configured such that gel stored in the storage container is expelled when the electrode is biased radially inward in contact with the skin of a patient. A processor may be employed to process the voltage measurements taken by the voltage measurement device and to generate a current density distribution in the third plane corresponding to the voltage measurements. The processor may also be configured to generate an image corresponding to the current density distribution in the third plane, the image having an improved resolution compared to conventional electrical impedance tomography systems.

Furthermore, in one embodiment, the third set of electrodes is moveable in an axial direction between the first and second planes to various other planes, e.g., a fourth plane, a fifth plane, etc. The processor is further configured to process the voltage measurements taken by the voltage measurement device so as to generate a current density distribution in the various other planes. In addition, the processor is further configured to generate a three-dimensional image corresponding to the current density distribution between the first and second planes.

DETAILED DESCRIPTION

Figure 1:
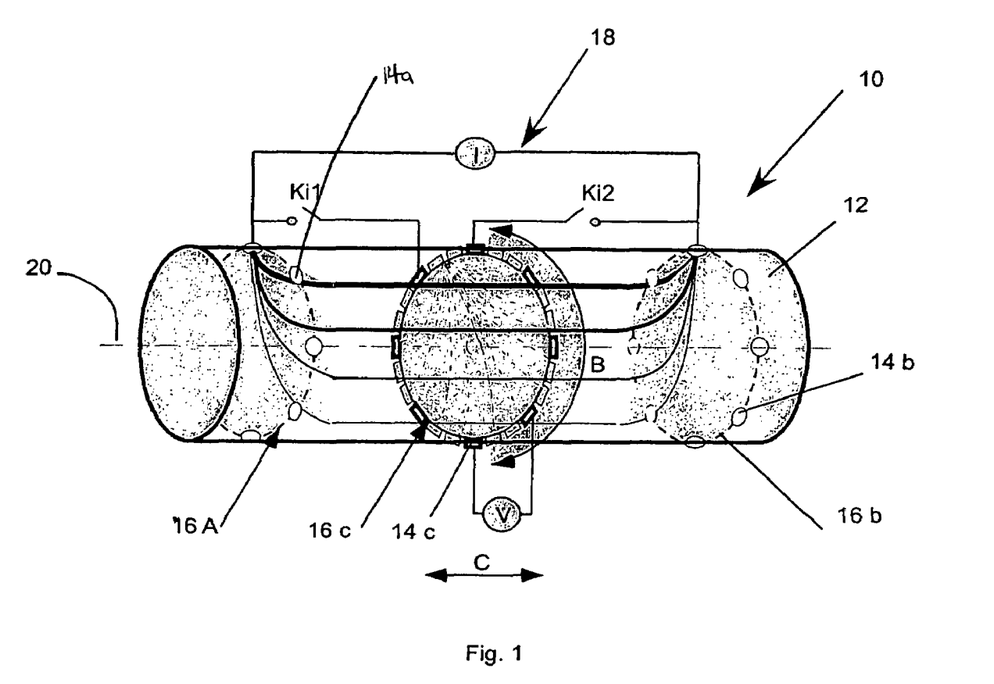
FIG. 1 illustrates schematically an imaging system, in accordance with one embodiment of the present invention.

FIG. 1 illustrates schematically an imaging system 10, in accordance with one embodiment of the present invention. The imaging system 10 is configured to provide an image corresponding to the conductivity distribution of a region 12, e.g., a vascular access. As shown in FIG. 1, the imaging system 10 provides electrodes 14 positioned in a plurality of planes 16 that intersect the region 12. For instance, the imaging system 10 may provide a first set of electrodes 14a that are located in a first current injection plane 16a. In addition, the imaging system 10 may provide a second set of electrodes 14b that are located in a second current injection plane 16b. The imaging system 10 may also provide a third set of electrodes 14c that are located in a measurement plane 16c, the measurement plane 16c being located in between the first and second current injection planes 16a, 16b. The electrodes 14a, 14b, 14c in the three different planes 16a, 16b, 16c are connected to each other by, and are controlled by, a control system 18, additional features of which are set forth in greater detail below.

The imaging system 10 is configured such that the third set of electrodes 14c are moveable within the measurement plane 16c. Specifically, the third set of electrodes 14c may be rotatable within the measurement plane 16c around a central axis 20 that is perpendicular to the measurement plane 16c. In addition, the imaging system 10 is configured such that the third set of electrodes 14c that are located in a measurement plane 16c are moveable relative to the first and second sets of electrodes 14a, 14b. Specifically, the third set of electrodes 14c may be moveable in an axial direction, e.g., perpendicular to the measurement plane 16c, relative to the first and second sets of electrodes 14a, 14b.

Figure 2A:
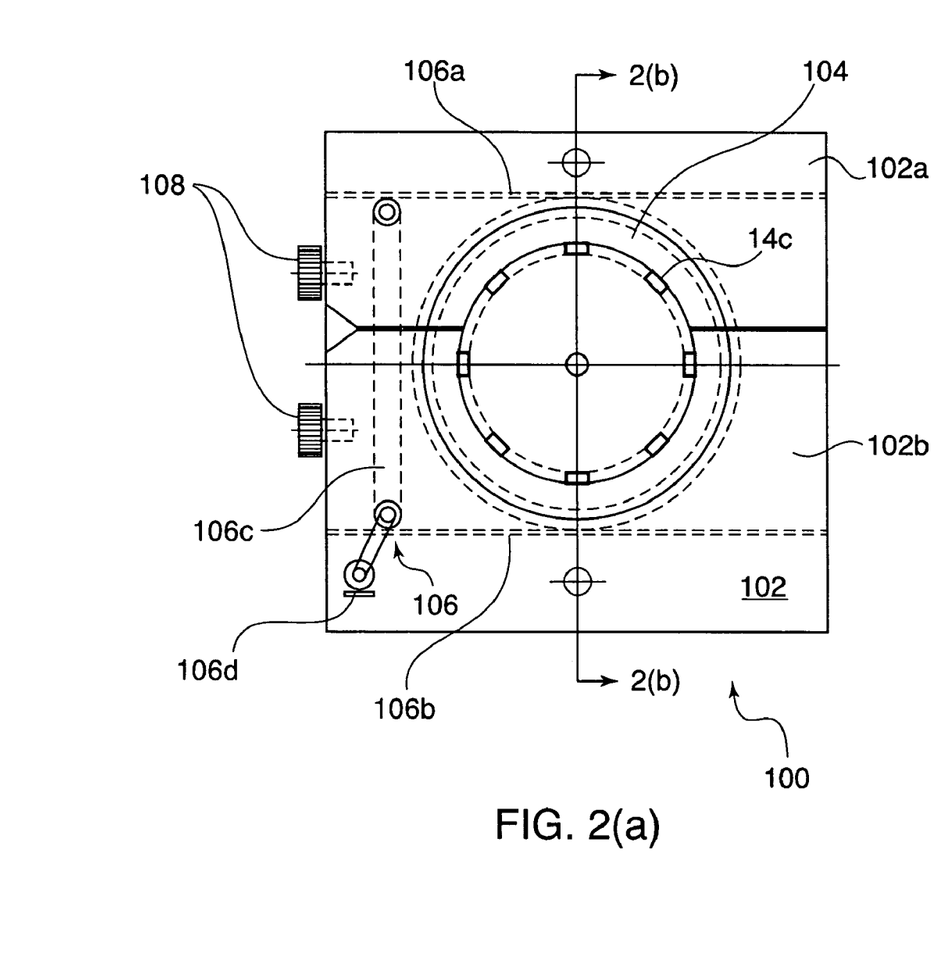
FIG. 2(a) illustrates an electrode arrangement for the third set of electrodes, according to one embodiment of the present invention.
Figure 2B:
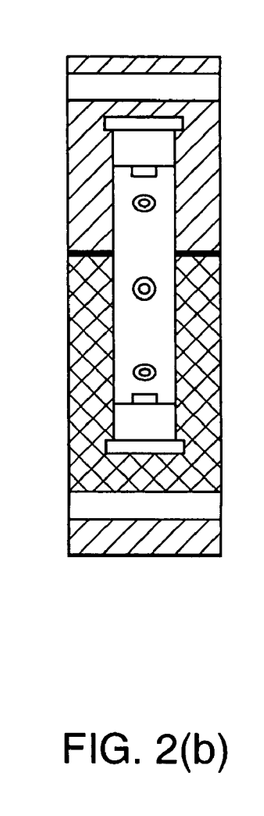
FIG. 2(b) is a cross-sectional view that illustrates the electrode arrangement of FIG. 2(a), taken along line 2(b)-2(b).

FIG. 2(a) illustrates a measurement electrode arrangement 100 for the third set of electrodes 14c, according to one embodiment of the present invention. FIG. 2(b) is a cross-sectional view that illustrates the measurement electrode arrangement 100 of FIG. 2(a), taken along line 2(b)-2(b). The measurement electrode arrangement 100 includes a housing 102 that is formed of an upper housing portion 102a and a lower housing portion 102b. Rotatably mounted within the housing 102 is an electrode supporting unit 104, additional details of which are set forth below. The electrode supporting unit 104 is configured to support the third set of electrodes 14c. The electrode supporting unit 104 is caused to rotate within the housing 102 by a driving arrangement 106. According to one embodiment, the driving arrangement 106 includes first, second and third driving bands 106a, 106b, 106c that are driven by a motor 106d. The driving arrangement 106, and particularly one or more of the driving bands 106a, 106b, 106c, is configured to engage the electrode supporting unit 104, and upon actuation of the motor 106d, to cause the electrode supporting ring 104 to rotate relative to the housing 102. While FIG. 2 illustrates a driving arrangement 106 that includes the driving bands 106a, 106b, 106c and a motor 106d, any driving arrangement that is capable of rotating the electrode supporting ring 104 relative to the housing 102 may be employed. The housing 102 may also include a pair of gears 108, the purpose of which is set forth in greater detail below.

Figure 3A:
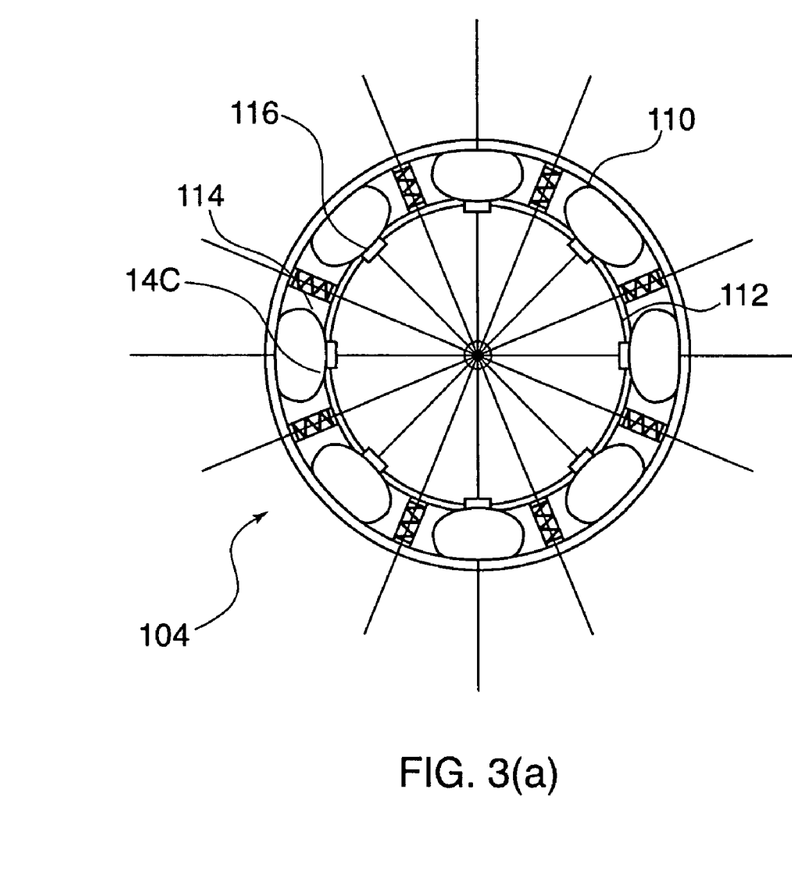
FIGS. 3(a) and 3(b) illustrate an electrode supporting unit for the third set of electrodes, according to one embodiment of the present invention, FIG. 3(a) being a cross-sectional view that illustrates the electrode supporting unit of FIG. 3(b), taken along line 3(a)-3(a).
Figure 3B:
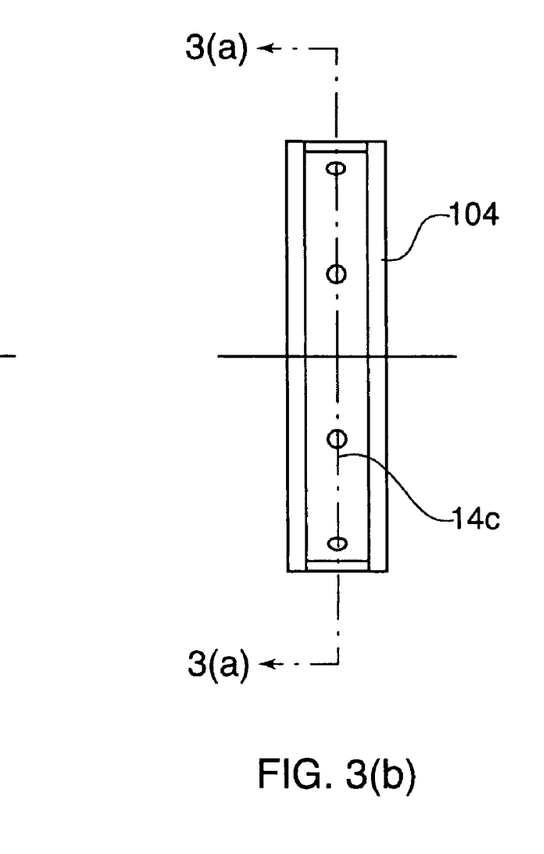

FIGS. 3(a) and 3(b) illustrate the electrode supporting unit 104 for the third set of electrodes 14c, according to one embodiment of the present invention. FIG. 3(a) is a cross-sectional view that illustrates the electrode supporting unit 104 of FIG. 3(b), taken along line 3(a)-3(a). The electrode supporting ring 104 includes an outer ring 110 and an inner ring 112. Mounted on and supported by the inner ring are the third set of electrodes 14c. The inner ring 112 is configured to be radially adjustable. Specifically, located between the outer ring 110 and the inner ring 112 are a first biasing element 114 and a second biasing element 116. The first biasing element 114 is configured to bias the inner ring 112 towards the outer ring 110, e.g., such that the inner ring is moved radially outward. According to one embodiment, the first biasing element is a spring. The second biasing element 116 is configured to bias the inner ring 112 away from the outer ring 110, e.g., such that the inner ring is moved radially inward. According to one embodiment, the second biasing element 116 is a series of inflatable balloons or the like.

Figure 4A:
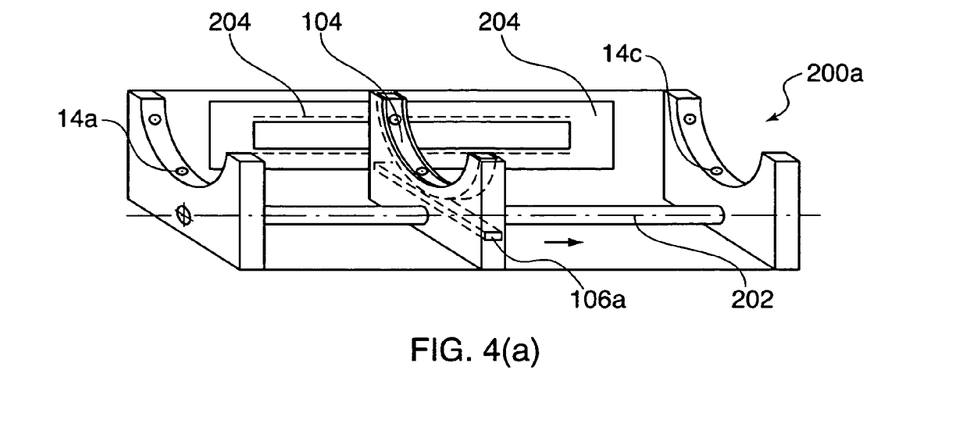
FIGS. 4(a) and 4(b) illustrate an imaging device, according to one embodiment of the present invention.
Figure 4B:
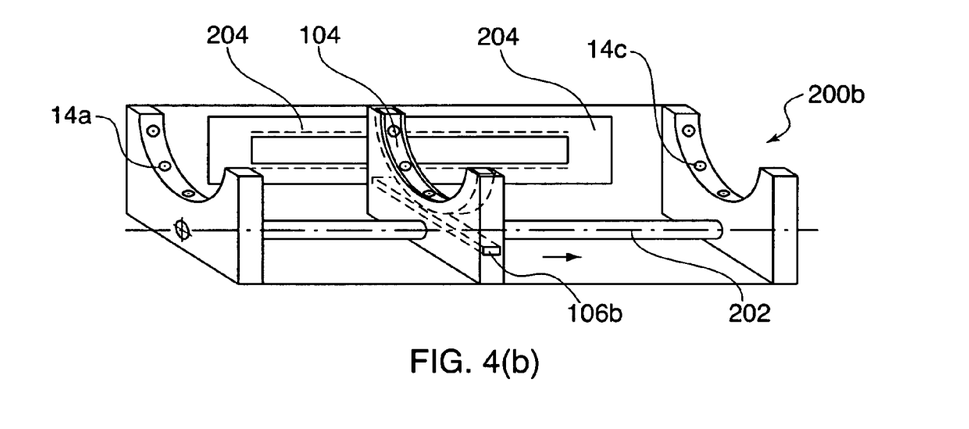

FIGS. 4(a) and 4(b) illustrate an imaging device 200, according to one embodiment of the present invention. Specifically, the imaging device 200 is a device for implementing the imaging system 10 as set forth more fully above. FIG. 4(a) illustrates an upper portion 200a of the imaging device 200, while FIG. 4(b) illustrates a lower portion 200b of the imaging device 200. The upper portion 200a and the lower portion 200b are advantageously configured to be combined so as to form the entire imaging device 200. When combined, the upper and lower portions 200a, 200b of the imaging device 200 are positioned relative to each other such that the electrodes 14a of the upper portion 200a are aligned with the electrodes 14a of the lower portion, such that all of the electrodes 14a are positioned within a single plane, e.g., the first current injection plane 16a. Likewise, when combined, the upper and lower portions 200a, 200b of the imaging device 200 are positioned relative to each other such that the electrodes 14b of the upper portion 200a are aligned with the electrodes 14b of the lower portion, such that all of the electrodes 14b are positioned within a single plane, e.g., the second current injection plane 16b. In addition, when combined, the upper housing portion 102a of the housing 102 is connected to the lower housing portion 102b of the housing 102, such that the electrodes 14c of the upper housing portion 102a are aligned with and positioned within a single plane, e.g., the measurement plane 16b, relative to the electrodes 14c of the lower housing portion 102b.

FIGS. 4(a) and 4(b) also illustrate additional features of the imaging device. For instance, each of the upper and lower portions 200a, 200b of the imaging device 200 have an axially extending slide bar 202 that engages a hole in the upper and lower housing portions 200a, 200b. In addition, each of the upper and lower portions 200a, 200b of the imaging device 200 have an axially extending gear arrangement 204 that engages one of the gears 108 of the housing 102. In operation, e.g., when the upper and lower housing portions 102a, 102b are combined, the gear arrangements 204 cause the respective upper and lower housing portions 102a, 102b to move axially along the slide bars 202, such that the entire housing 102 moves axially along the imaging device 200. While FIGS. 4(a) and 4(b) illustrate a gear arrangement 204 for axially moving the upper and lower housing portions 102a, 102b, any moving or driving arrangement that is capable of moving the upper and lower housing portions 102a, 102b relative to the first and second current injection planes 16a, 16b may be employed.

Figure 5:
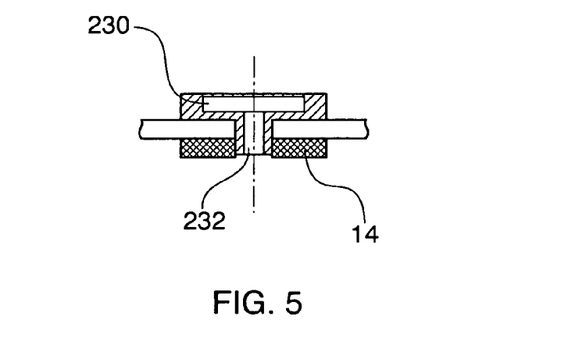
FIG. 5 is a cross-sectional view that illustrates an electrode, according to one embodiment of the present invention.

FIG. 5 is a cross-sectional view that illustrates an electrode, e.g., electrodes 14a, 14b, 14c, according to one embodiment of the present invention. The electrodes 14 may be comprised of AgCl. The electrodes 14 may also include a gel storage container 230 for storing conductive gel. The gel stored within the gel storage container 230 is squeezed or otherwise expelled by the second biasing element, e.g., the balloon, along a small channel 232 to, e.g., the skin of a patient. According to this embodiment, the electrodes 14 are configured to obtain lower electrode-skin contact impedance as compared to conventional electrodes.

Figure 6:
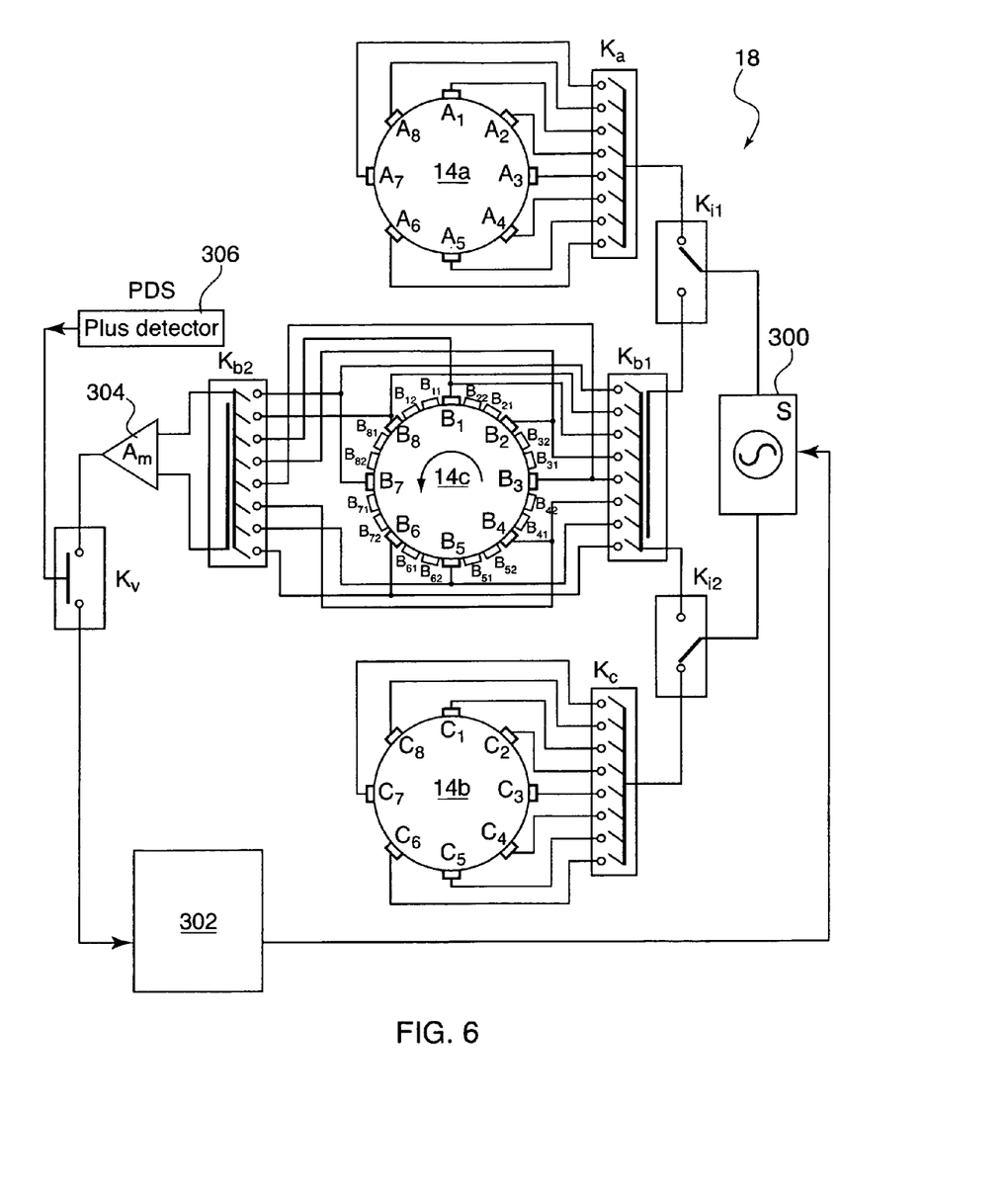
FIG. 6 is a schematic diagram that illustrates the circuit of the electrical impedance tomography imaging system, in accordance with one embodiment of the present invention.

FIG. 6 is a schematic diagram that illustrates a control circuit 18 of the electrical impedance tomography imaging system 10, in accordance with one embodiment of the present invention. The three sets of electrodes 14a, 14b, 14c are connected to a current source 300 that provides a multi-frequency current under the control of a processor 302, e.g., a computer. The processor 302 is configured to control the various components of the control circuit 18 in accordance with a predetermined algorithm, set forth in further detail below. The first set of electrodes 14a includes electrodes A1 to A8 each of which is selectively connected to the current source 300 by switch Ka. Likewise, the second set of electrodes 14b includes electrodes C1 to C8, each of which is selectively connected to the current source 300 by switch Kc. In this manner, switches Ka and Kc are employed to change the pairs of electrode via which current is injected. In addition, the third set of electrodes 14c includes electrodes B1 to B8, each pair of electrodes having two electrodes, e.g., electrode B11, B12, etc., positioned therebetween. The electrodes B1 to B8 are connected to switches Kb1 and Kb2, which selectively connect these electrodes to an amplifier 304 for measuring the voltage across the selected electrodes. The measurement of the voltage is controlled by a plus detector 306, which controls a switch Kv for transmitting the voltage measurements to the processor 302.

In operation, the imaging device 200 is positioned such that a patient's body part, e.g., an arm having a vascular access, is disposed in a generally axial direction intersecting the three planes 16a, 16b, 16c and within the three sets or rings of electrodes, 14a, 14b, 14c. In the embodiment shown in FIG. 4, the patient's body part may be positioned in the lower portion 200b of the imaging device 200, and the upper portion 200b may then be placed onto the lower portion 200b such that the respective sets of electrodes are aligned relative to each other. The processor 302, in accordance with a predetermined algorithm, selectively operates the switches Ka and Kb so that multi-frequency current is injected via a first electrode of the first set of electrodes 14a and a first electrode of the second set of electrodes 14b. The processor 302 may continue to selectively operate the switches Ka and Kb in accordance with the predetermined algorithm so that multi-frequency current is injected via the other electrodes of the first set of electrodes 14a and the other electrodes of the second set of electrodes 14b.

In addition, the processor 302, in accordance with the predetermined algorithm, selectively operates the switches Kb1 and Kb2 so as to measure voltage between a first electrode, e.g., B1, of the third set of electrodes 14c and a second electrode, e.g., B2, of the third set of electrodes 14c. The processor 302 may continue to selectively operate the switches Kb1 and Kb2 in accordance with the predetermined algorithm so as to measure voltage between the other electrodes of the third set of electrodes 14c. After an initial voltage measurement has been performed, the electrode supporting unit 104 that supports the third set of electrodes 14c is caused to rotate. Specifically, the processor 302 is configured to send signals to the driving arrangement 106 of the housing 102 in order to operate the driving arrangement 106 and cause the rotation of the electrode supporting unit 104. In the embodiment shown, wherein the third set of electrodes 14c includes 24 electrodes, the processor 302 may be configured to rotate the electrode supporting unit 104 by 15 degrees, although other amounts of rotation may be performed. Once rotated, the processor 302 may, in accordance with the predetermined algorithm, selectively operate the switches Kb1 and Kb2 so as to measure voltage between an electrode, e.g., B11, of the third set of electrodes 14c and another electrode, e.g., B81, of the third set of electrodes 14c. The processor 302 may continue to selectively operate the switches Kb1 and Kb2 in accordance with the predetermined algorithm so as to measure voltage between other electrodes of the third set of electrodes 14c. The electrode supporting unit 104 that supports the third set of electrodes 14c may then be rotated again so as to continue performing voltage measurements between the respective electrodes until, for instance, a total of 24 position voltages are measured across the third set of electrodes 14c. Advantageously, since a blood volume may have a high conductance compared to other body tissues, the voltage is measured using a signal synchronized with the R wave of an electrocardiogram, e.g., a tall wave in the QRS complex of an electrocardiogram. In this manner, each voltage measurement is made in the same hemodynamic condition, with or without blood in the blood vessel, and thus improves the estimation of resistivity distribution.

According to one embodiment, the processor 302 is configured to process the various voltage measurements taken by the voltage measurement device so as to generate a current density distribution in the third plane 16c, as set forth more fully below. Furthermore, the processor 302 may be further configured to generate an image corresponding to the current density distribution in the third plane 16c. The image generated by the processor 302 provides an improved resolution that enables an operator to more accurately and reliably monitor the vascular access.

Contact impedance between the electrodes and a patient's skin is an important factor which may affect the measurement of internal resistivity. Specifically, if one or more of the electrodes 14 are not fully in contact with the skin of a patient during a voltage measurement, the voltage measurement may be erroneous. The present invention ensures that the electrodes 14 are fully in contact with the skin of the patient. For instance, when a voltage measurement is to be taken, the processor 302 is configured to expand the second biasing elements 116, e.g., the balloons, so as to cause the electrodes 14 to fully contact the skin of the patient. To insure that the electrodes are fully in contact with the skin, a pressure in the balloon may be measured and may be increased or decreased as necessary. If the processor 302 determines that the individual pressure of a balloon is outside of a predetermined pressure range—and therefore that the electrode 14 which is moved by that balloon is not fully in contact with the skin—an alerting mechanism, e.g., a visual indicator, an audible alarm, etc., may be employed to alert the operator before the voltage measurement is taken. When the electrode supporting unit 104 is required to be moved or rotated, the balloons may be deflated sufficiently such that the first biasing element 114, e.g., the spring, may overcome the force exerted by the balloon, thereby moving the electrodes 14 away from the skin of the patient. Once the electrode supporting ring 104 is rotated and in a next desired position, the balloons may be pressurized again so as to bring the electrodes into full contact with the skin again.

The above-described method provides a current density distribution at a specific plane between the first and second current injection planes 14a and 14b. In this manner, a two-dimensional image may be generated based upon the voltage measurements obtained via the third set of electrodes 14c at the measurement plane 16c. In order to generate a three-dimensional image between the first and second current injection planes 14a and 14b, the electrode supporting unit 104 that includes the third set of electrodes 14c may be moved to various different positions between the first and second current injection planes 14a and 14b. At each of the various positions, a current density distribution may be obtained according to the above-described method. Once a current density distribution has been obtained at a plurality of locations between the first and second current injection planes 14a and 14b, the processor 302 may generate a three-dimensional image corresponding thereto.

Figure 7:
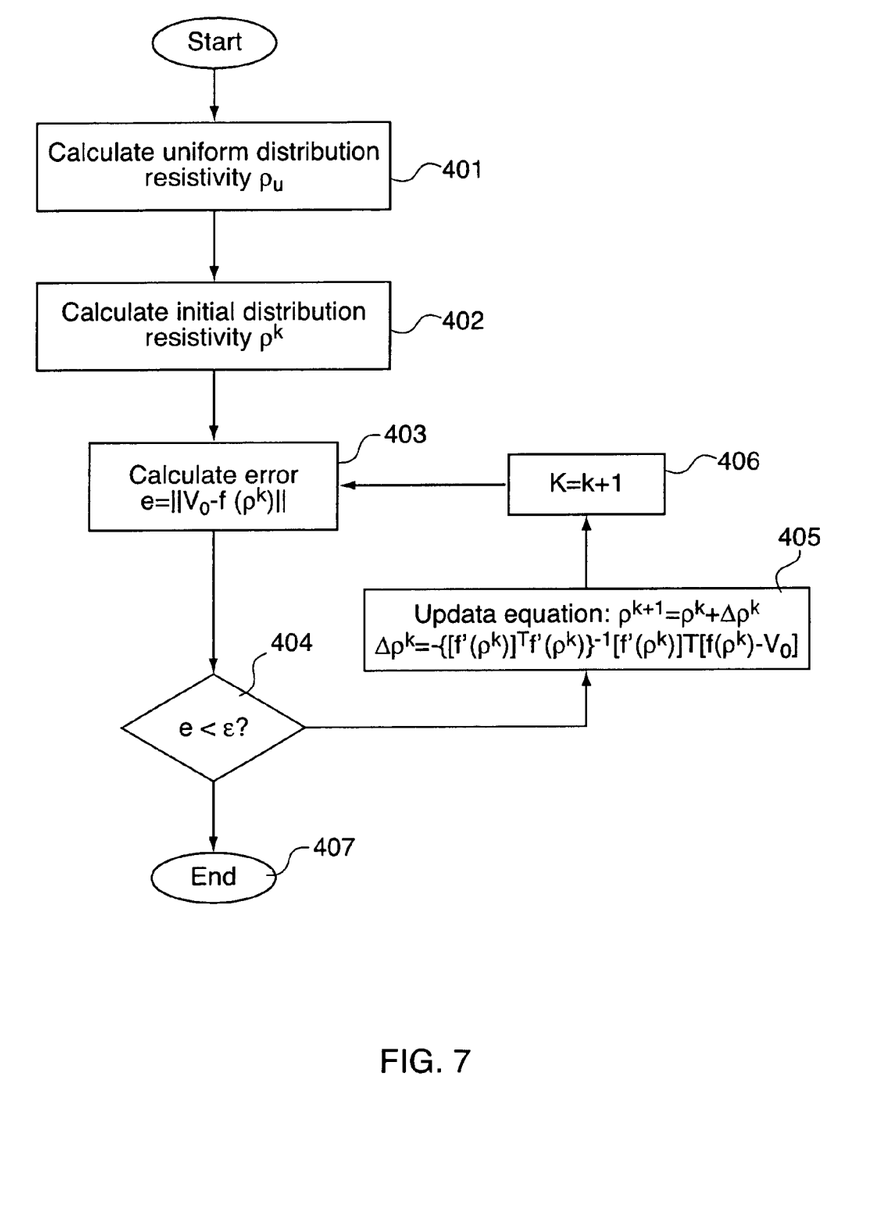
FIG. 7 is a flowchart that illustrates the steps performed by an algorithm of the processor, according to one embodiment of the present invention.

FIG. 7 is a flowchart that illustrates the steps performed by an algorithm of the processor 302, according to one embodiment of the present invention to generate an image corresponding to a conductivity distribution. Generally, an initial resistivity is measured, unlike conventional electrical impedance tomography algorithms which typically merely employ an informed guess of the initial resistivity. After the initial resistivity is measured, a Newton-Raphson algorithm is performed to calculate distribution of resistivity. The Newton-Raphson algorithm is described in detail in J. G. Webster, ED, Electrical Impedance Tomography, Bristol, Mass.: Adam Hilger, 1990, which is incorporated herein fully by reference.

More specifically, at step 401, the processor 302 calculates a uniform distribution resistivity. For instance, in the measurement plane 16c, the resistivity in the same plane ($\rho_{xy}$) is calculated by the measurement of the voltage between any two electrodes of the measurement plane 16c when current is injected from any two electrodes of current injecting planes 14a, 14b. A cycle may be performed such that measurements are made corresponding to each of the, e.g., eight electrodes, so as to form a uniform current density when current electrodes are in the same side as measuring electrodes. It also produces a non-uniform current density when the current electrodes are positioned on opposite sides of measuring electrodes. More specifically, when current is injected by electrodes, e.g., electrodes A1 and B1, the voltage measured between, e.g., electrodes C1 and C2, is expected to be similar to the voltage measured between, e.g., electrodes C8 and C1, if the resistivity in the measurement plane 14c is homogenous. Therefore, by using electrodes in the two current injecting planes, e.g., planes 14a, 14b, that are in the same relative position, for instance, electrode A1 and electrode B1, electrode A2 and electrode B2, etc., through electrode A8 and electrode B8, a uniform distribution resistivity can be obtained. When changing the order of electrode pairs so as to not use electrodes in the same relative position, such as electrode A1 from the first currenting injecting plane 14a and electrode B8 from the second current injecting plane 14b, the current distribution in the measurement plane 14c may be different to the current distribution when electrodes in the same relative position, e.g., electrodes A1 and B1, are used. In this manner, the imaging system 10 of the present invention, in accordance with one embodiment, may provide more detailed information concerning the resistivity in the measurement area while increasing the number of independent components to calculate a particular resistivity distribution, thereby improving the resolution of the image generated thereby.

According to the back-projection method mentioned above, the uniform resistivity can be calculated by $$R(\rho_u)=B(V/I) \quad \text{Eq. 1}$$

where $R(\rho_u)$ is the uniform resistivity represented by resistance (R), B is the weighting matrix and V and I are the voltage and current on the surface.

At step 402, a filtered back-projection algorithm is used to calculate initial resistivity distribution as follows:

$$\Delta\rho=(S^TS)^{-1}S^T(V_0-V_m) \quad \text{Eq. 2}$$

$$\rho=\rho_u+\Delta\rho \quad \text{Eq. 3}$$

where S is sensitivity matrix, $V_0-V_m$ are voltage at calculation and measurement on the skin surface. The sensitivity matrix S can be generally written as $$S_{i,j} = \int_{element} \nabla\Phi \cdot \nabla\Psi dv \quad \text{Eq. 4}$$

where $\nabla\phi$ and $\nabla\psi$ are the current distribution and the potential field, respectively. Using Equations 1 and 3, the initial resistivity is calculated for step 402 to generate or reconstruct the electrical impedance tomography image.

At steps 403 to 406, the processor 302 employs the Newton-Raphson algorithm. According to the Newton-Raphson algorithm, there is found a minimal error (e(ρ)) between a measured voltage and a calculated voltage from the internal resistivity distribution by the following equation:

$$e(\rho)=[f'(\rho)]^T[f(\rho r)-V_0]=0 \quad \text{Eq. 5}$$

where f (ρ) is the estimation of voltage according to resistivity distribution and the Jocobian matrix given by the following equation:

$$[f'(\rho)]_{ij}=\partial f_i/\partial \rho_j \quad \text{Eq. 6}$$

As previously set forth above, three-dimensional electrical impedance tomography is obtained by moving the measurement plane 16c to various different axial locations, and by performing the same two-dimensional processing as set forth above at each of the different axial locations. Continuous monitoring of the patient may be performed using a multi-frequency, back-projection algorithm based on the processing performed above in accordance with step 401.

The imaging system 10 of the present invention provides a device, e.g., imaging device 200, that may be employed in a clinical environment for continuously monitoring the vascular access of a patient. As previously set forth, the inside of a patient's body has a complex distribution of conductivity, such that current passes into the body nonlinearly in a measured plane, e.g., the measurement plane 16c. Additionally, the density of current in the body decreases with the increase in the distance between the points of injection of current and the measurement of voltage. The present invention addresses the problems that result from these phenomenon by producing a homogenous electrical current density in the axial direction between the first and second current injecting planes 14a, 14b. Since biological tissue has an inhomogeneous conductivity distribution, in the measurement plane, a difference in the measured voltage between each two adjacent electrodes provide an indication that the distribution of conductivity is in fact due to the different components of body composition.

While conventional electrical impedance tomography systems suggest an increase in the number of points of measurement in order to try to improve the resolution of the generated image, the number of electrodes that may be employed in an electrical impedance tomography system is limited by the circumference of a patient's limb or body part to be measured. Furthermore, the greater the number of electrodes that are used, the smaller the area that can be measured by the electrode and the smaller the distance between adjacent electrodes, both of which are factors that are known to significantly increase the voltage measurement error. The present invention, on the other hand, provides a system whereby a third set of electrodes 14c in the measurement plane 16c may be rotated between measurements, enabling fewer electrodes to be employed and thereby improving the accuracy of the voltage measurements taken and the resolution of the image generated therefrom.

Furthermore, while there are various patents and articles which propose methods by which three-dimensional electrical impedance tomography may be performed, each of the described methods provides for three or more sets of electrodes in three or more measurement planes, wherein each of the sets of electrodes are positioned in close proximity relative to each other. The large number of electrodes positioned in close proximity to each other causes additional measurements errors. The present invention, on the other hand, provides a system and method for generating a three-dimensional electrical impedance tomography image, whereby a single set of electrodes, e.g., the third set of electrodes 14c, is moveable between the first and second current injecting planes 14a, 14b. Thus, the system of the present invention decreases the number of electrodes that are required to be employed in the space between the first and second current injecting planes 14a, 14b, thereby improving the accuracy of the measurements taken and the resolution of the three-dimensional image generated therefrom. Still another advantage of the system and method of the present invention is that, by virtue of the first and second biasing elements, full contact between the electrodes and the skin of a patient may be insured, thereby further improving the accuracy of the measurements taken and the resolution of the image generated therefrom.

Thus, the system and method of the present invention, by measuring and monitoring a vascular access in a hemodialysis patient for the purpose of generating an image of the vascular access, enables a determination at an early stage when, e.g., a thrombosis, of the vascular access has occurred. In addition, the present invention may also be employed to measure and monitor vessels in other body parts, e.g., a portion of a leg such as a calf, to determine whether there exists a venous thrombosis—a common clinical problem experienced by patients. Still further, the system and method of the present invention may be employed for detecting stiffness of blood vessels of atherosclerotic plaques, or may be employed to generate an image of a patient's chest if sized appropriately.

Thus, the several aforementioned objects and advantages of the present invention are most effectively attained. Those skilled in the art will appreciate that numerous modifications of the exemplary embodiment described hereinabove may be made without departing from the spirit and scope of the invention. Although a single exemplary embodiment of the present invention has been described and disclosed in detail herein, it should be understood that this invention is in no sense limited thereby and that its scope is to be determined by that of the appended claims.

What is claimed is:

1. A system for performing electrical impedance tomography comprising:
 a housing having a longitudinal axis;
 a first set of electrodes positioned in a first plane, the first plane intersecting the longitudinal axis;
 a second set of electrodes positioned in a second plane, the second plane being different from the first plane and intersecting the longitudinal axis; and
 a third set of electrodes positioned in a third plane, the third plane intersecting the longitudinal axis between the first and second planes, and being distinct from the first plane and the second plane,
 wherein the third set of electrodes is rotatable around the longitudinal axis relative to the first set of electrodes and the second set of electrodes.

2. The system of claim 1, further comprising a current source configured to inject current between at least one electrode of the first set of electrodes and at least one electrode of the second set of electrodes.

3. The system of claim 2, further comprising one or more switches that are configured to selectively connect each one of the electrodes of the first set of electrodes to each one of the electrodes of the second set of electrodes.

4. The system of claim 3, further comprising a processor configured to control the switches.

5. The system of claim 2, wherein the current is a multi-frequency current.

6. The system of claim 1, further comprising a current source configured to inject current between a first electrode of the third set of electrodes and a second electrode of the third set of electrodes.

7. The system of claim 6, further comprising one or more switches that are configured to selectively connect the electrodes of the third set of electrodes to the other electrodes of the third set of electrodes.

8. The system of claim 7, further comprising a processor configured to control the switches.

9. The system of claim 1, further comprising a voltage measurement device configured to measure voltage between a first electrode of the third set of electrodes and a second electrode of the third set of electrodes.

10. The system of claim 9, further comprising one or more switches that are configured to selectively connect the electrodes of the third set of electrodes and the other electrodes of the third set of electrodes to the voltage measurement device.

11. The system of claim 10, further comprising a processor configured to control the switches.

12. The system of claim 9, wherein the voltage measurement device is an amplifier.

13. The system of claim 9, further comprising a processor configured to process the voltage measurements taken by the voltage measurement device so as to generate a current density distribution in the third plane.

14. The system of claim 13, wherein the processor is further configured to generate an image corresponding to the current density distribution in the third plane.

15. The system of claim 13, wherein the third set of electrodes is moveable in an axial direction between the first and second planes to a fourth plane.

16. The system of claim 15, wherein the processor is further configured to process the voltage measurements taken by the voltage measurement device so as to generate a current density distribution in the fourth plane.

17. The system of claim 16, wherein the processor is further configured to generate a three-dimensional image corresponding to the current density distribution between the first and second planes.

18. The system of claim 16, wherein the voltage measurement device is configured to measure voltage using a signal synchronized with the R wave of an electrocardiogram.

19. The system of claim 1, wherein the third set of electrodes is supported by an electrode supporting unit.

20. The system of claim 19, wherein the electrode supporting unit includes a first biasing element for biasing the electrodes radially inward when a measurement is to be taken and a second biasing element for biasing the electrodes radially outward when the electrode supporting unit is to be moved or rotated.

21. The system of claim 20, wherein the electrode includes a storage container for conductive gel, and the electrode is configured such that gel stored in the storage container is expelled when the electrode is biased radially inward.

22. The system of claim 20, wherein the first biasing element is a spring.

23. The system of claim 20, wherein the second biasing element is a balloon.

24. The system of claim 20, wherein the electrode supporting unit comprises an inner ring and an outer ring, and the first biasing element and second biasing element are located between the inner ring and the outer ring.

25. The system of claim 1, wherein the first, second and third sets of electrodes are mounted on upper and lower portions of an imaging device, the upper and lower portions being separable so as to enable a patient body part to be placed between the upper and lower portions.

26. The system of claim 1, wherein the housing further comprises an electrode supporting unit configured to support the third set of electrodes.

27. The system of claim 1, wherein the third set of electrodes is moveable along the longitudinal axis in an axial direction between the first plane and the second plane.

28. The system of claim 1, wherein the first set of electrodes and the second set of electrodes are disposed within the housing, the housing including an opening configured to receive a body part wherein the body part intersects the first plane, the second plane and the third plane when placed within the opening and the third set of electrodes is rotatable around the body part.

29. The system of claim 28, wherein the body part is one of a leg, an arm and a calf.

* * * * *